(12) United States Patent
Kessler

(10) Patent No.: US 6,261,577 B1
(45) Date of Patent: Jul. 17, 2001

(54) NON-STAINING TOPICAL IODINE COMPOSITION AND METHOD

(75) Inventor: Jack Kessler, Southborough, MA (US)

(73) Assignee: Symbollon Corporation, Framingham, MA (US)

(*) Notice: Subject to any disclaimer, the term of this patent is extended or adjusted under 35 U.S.C. 154(b) by 0 days.

(21) Appl. No.: 09/201,338

(22) Filed: Nov. 30, 1998

Related U.S. Application Data

(63) Continuation-in-part of application No. 08/895,362, filed on Jul. 16, 1997, now abandoned.

(51) Int. Cl.$^7$ .............................. A61K 7/48; A61K 9/00; A61K 33/18

(52) U.S. Cl. .................. 424/401; 424/78.07; 424/443; 424/667; 514/772.2; 514/772.3; 514/781; 514/782; 514/784; 514/928

(58) Field of Search .................... 424/401, 669, 424/405, 78.02, 78.07, 78.06, 667, 443, 78.03; 514/928, 887

(56) References Cited

U.S. PATENT DOCUMENTS

| | | | |
|---|---|---|---|
| 2,739,922 | 3/1956 | Shelanski | 167/70 |
| 3,028,299 | 4/1962 | Winicov et al. | 167/17 |
| 3,728,449 | 4/1973 | Cantor et al. | 424/150 |
| 4,271,149 * | 6/1981 | Winicov et al. | 424/150 |
| 4,849,215 * | 7/1989 | Gottardi | 424/80 |
| 4,954,351 * | 9/1990 | Sackler et al. | 424/80 |
| 5,173,291 | 12/1992 | Brink et al. | 424/78.06 |
| 5,368,868 | 11/1994 | Winicov | 424/667 |
| 5,503,838 | 4/1996 | Schmidt et al. | 424/407 |
| 5,529,770 | 6/1996 | McKinzie et al. | 424/667 |

OTHER PUBLICATIONS

Gottardi W. The formation of iodate as a reason for the decrease of efficiency of iodine containing disinfectants, Zbl Bakr Hyg 1981;1 (Abt Orig B) 172, 498–507. Abstract Only.

Gottardi W. Iodine and iodine compounds. In Disinfection, Sterilization and Preservation, 4th Ed. 1991, pp. 152–166, (SS Block Ed.), Lea & Febiger, Philadelphia.

Rodeheaver G. Bellamy W, Kody M, Spatafora G, Fitton L., Leydon K, Edlich R. Bactericidal activity of toxicity of iodine–cleaning solutions in wounds. Arch. Surg. 1982; 117:181.

Allawala NA, Riegleman S. The properties of iodine in solutions of surface active agents. J Am. Pharm. Assoc. 1953; XLII:396–401.

Gottardi W. The uptake and release of molecular idoien by the skin; chemical and bactericidal evidence of residual effects caused by povidone–iodine preparations. J. Hosp. Infec. 1952; 29:9–18.

* cited by examiner

*Primary Examiner*—James M. Spear
(74) *Attorney, Agent, or Firm*—Anderson, Kill & Olick, P.C.

(57) ABSTRACT

Non-staining topical iodine disinfecting compositions having the ability to inactivate pathogens associated with skin infections or diseases. based upon the presence of molecular iodine in a concentration above at least 15 ppm. Any other iodine species selected from the group consisting of complexed iodine and triiodide may be present with the total of such other iodine species limited to a concentration of less than about 700 ppm so that any visible stain resulting from the application of this composition on the skin will dissipate without leaving any visible skin coloration.

15 Claims, No Drawings

NON-STAINING TOPICAL IODINE COMPOSITION AND METHOD

This application is a continuation-in-part of parent application U.S. Ser. No. 08/895,362 filed Jul. 16, 1997, now abandoned.

FIELD

This application describes a method of topically treating skin with iodine to kill pathogens in and on the epidermal surface of the skin without irritating the skin and without leaving a visable skin discoloration and to non-staining topical iodine compositions that provide antimicrobial persistence for the disinfection of topical pathogens and for treatment and/or prevention of skin infections and diseases.

BACKGROUND OF INVENTION

Tincture of iodine was first used as a topical disinfectant in 1839. Tincture of iodine and subsequent iodine compositions, like Lugol's solution, are topical irritants that stain human skin. The invention of povidone iodine in 1956 (U.S. Pat. No. 2,739,922), commonly referred to as "tamed" iodine, eliminated the topical irritancy associated with iodine but not the staining.

Povidone iodine contains very low (1–10 ppm) concentrations of molecular iodine ($I_2$) and high concentrations of triiodide ($I_3^- \approx 10,000$ ppm) and iodide ($I^- \approx 5,000$ ppm). Such compositions are referred to as "complexed" iodine. Complexed iodine generically refers to compositions wherein molecular iodine is complexed with organic molecules and/or iodide. Molecular iodine is complexed in order to increase shelf-life and reduce irritation. It is currently described in the literature and believed by those skilled in the art that molecular iodine is the iodine species responsible for epidermal irritancy and staining. By lowering the concentration of molecular iodine it is believed that the irritancy and staining of iodine is minimized.

Many inventions that rely upon complexed iodine have been made in the field of topical iodine compositions. Iodine is complexed by contacting a source of diatomic iodine ($I_2$) with a polymeric material having large segments of polymeric residues derived from ethylene oxide, propylene oxide or other alkylene oxides in the form of block polymer chains. Examples include ethoxylated surfactants, cellulose, cellulose derivatives and polyvinyl pyrrolidone components. The alkoxylated (usually ethoxylated) surfactants include, but are not limited to, the group consisting of alkylphenol ethoxylates, ethoxylated fatty acids, alcohol ethoxylates, alcohol alkoxylates, polysorbates (ethoxylated sorbitol) and ethylene oxide-propylene oxide copolymers (commonly called Poloxamers as described in U.S. Pat. No. 5,368,868). A preferred source of iodine for reaction with nonionic materials to form iodine complexes is a composition comprising iodine in association with an inorganic iodide which provides a source of "active" iodine. Such a source is described in Winicov, U.S. Pat. No. 3,028,299, Cantor et. al. U.S. Pat. No. 3,728,449, Schmidt W. et. al. U.S. Pat. No. 5,503,838, Brink et al. U.S. Pat. No. 5,173,291, and McKinzie M. et al., U.S. Pat. No. 5,529,770. Commonly, at least 0.35 parts of iodide ($I^-$) are present per part of diatomic iodine.

Topical application of biocidal agents has been accomplished using solutions, ointments and physical appliances. To provide prolonged antisepsis, it is usually necessary to repeatedly apply an iodine topical agent since microorganisms may survive the initial application. Topical iodine biocides are usually water soluble which leads to their removal from the epidermis by contact with water or bodily fluids. Increasing the water and bodily fluid resistance of topically applied iodine agents and thereby increasing the substantivity and length of bactericidal activity has been a long-standing goal in the art. This invention teaches against compositions that impart a highly visible iodine coloration to the epidermis such as that derived from complexed iodine and further discloses formulation constraints to provide a persistent non-irritating topical iodine disinfectant that does not stain. Such compositions have several commercially useful properties. The iodine compositions of this invention are not materially affected by water and body fluids and provide long lasting efficacy. Also, the compositions of this application provide iodine in a form that is capable of penetrating the skin and inactivating pathogens that reside within and on the skin.

SUMMARY OF THE INVENTION

The term "molecular iodine" as used herein refers to diatomic iodine, which is represented by the chemical symbol $I_2$, which is not complexed with other molecules so that it is free to diffuse into epidermal tissue.

The term "complexed iodine" as used herein, refers to free molecular iodine that is combined with an organic carrier or with iodide anions to form triiodide such that the chemical activity of free molecular iodine is reduced. The complexed iodine is preferably prepared by combining diatomic iodine and a complexing agent.

The term "iodide anion" as used herein, refers to the species that is represented by the chemical symbol $I^-$. Suitable counter-ions for the iodide anion include sodium potassium and the like.

The term "triiodide" as used herein, refers to the species which is represented by the chemical symbol $I_3^-$. It is recognized by one skilled in the art that triiodide can dissociate into one iodide anion and one molecule of free molecular iodine.

The term "total iodine" as used herein, refers to the following iodine species: free molecular iodine, iodide, organically complexed forms of iodine and triiodide.

The term "rate of iodine generation" as used herein, refers to the rate at which molecular iodine is formed.

The term "ratio of molecular iodine" as used herein, refers to the ratio of molecular iodine ($I_2$) to other iodine species such as iodide and triiodide.

It has been believed that molecular iodine is an irritant and responsible for the staining of skin associated with the use of topical iodine compositions. We have observed that complexed iodine, not molecular iodine, is the species of iodine that is primarily responsible for skin staining in commercially available iodine compositions. We have further observed that it is possible to formulate compositions that will deliver molecular iodine into the epidermis and not stain or irritate skin. Once molecular iodine penetrates into the skin, it maintains its biocidal activity while in the skin and can diffuse back out of the skin (W. Gottardi, *Journal of Hospital Infection*, Vol. 29, page 9, 1995). Such back-diffusion provides a long-lived chemical barrier that is resistant to water and body fluids.

This application describes the formulation constraints necessary to provide a topical iodine disinfectant that will not irritate or stain epidermal tissue but will otherwise kill pathogens on the epidermis; these formulation constraints apply to the following forms of iodine: molecular iodine, iodide, triiodide and complexed iodine. The teachings and examples in this application do not make any attempt to specifically enumerate all of the prior art in the area of topical iodine preparations. Excipients that are known to be compatible with complexed iodine may also be of use with compositions and conditions described in this application. Such excipients include surfactants, thickeners, film forming agents, penetrants, humectants, emollients, dyes, skin conditioning agents, stabilizing agents, opacifiers, wetting agents, chelating agents, buffers, organic acids and fragrances.

DESCRIPTION

Topical disinfectants are used to inactivate pathogenic organisms that are present on the epidermis and to prevent pathogenic organisms from populating the epidermis. A preferred topical disinfectant will (a) not irritate or stain the epidermis, (b) have a broad spectrum of activity, (c) rapidly inactivate pathogens, (d) provide residual activity for 2 to 8 hours, (e) resist water and bodily fluids, and (f) prevent pathogenic organisms from repopulating the epidermis. To date there are no perfect topical antimicrobial compositions in commerce. The compositions described in this application are based on defined ratios of free molecular iodine to total iodine and provide, in combination with other excipients, the basis for preferred topical disinfectants.

Iodine compositions, as compared to topical compositions based on other active agents, have a material disadvantage in that they stain skin. Typical iodine stains are reddish brown or yellowish in color and these stains do not readily dissipate from the epidermis. It has long been assumed that the form of iodine that stains the skin is molecular iodine. We have observed that this is not true and that most of the staining from iodine compositions is due to triiodide as demonstrated in the Examples of this application.

For purposes of this application, a stain is a yellowish-brown coloration of the skin that does not completely dissipate after a defined time period. The relevant time period for dissipation of a stain will vary with the intended application. For instance, if a topical disinfectant is applied to the faces of adolescent girls several times a day, then any coloration that may be present should dissipate within 1 minute. If a topical antifungal composition is formulated for use on toes and applied prior to sleeping then any coloration should dissipate within 6 hours. If a topical iodine composition is formulated for use on cow teats to prevent mastitis and applied after milking then coloration can remain for at least 30 minutes post application.

It is obvious to one skilled in the art that there is a wide variation between people with respect to the degree of staining their skin will experience from iodine-based topicals. We have also observed that the degree of staining is a function of the carrier that contains the iodine. For instance, isopropyl myristate, which facilitates the penetration of agents into the epidermis, reduces the degree of coloration from free molecular iodine. Also, the degree of staining from topical iodine compositions that are liquids is a function of the application time. The longer a liquid is in contact with the epidermis, the more pronounced the staining.

The most preferred compositions anticipated by this application will not produce any coloration of the epidermis. The preferred compositions of this application will produce a mild iodine coloration that is dissipated within 10 minutes. The range of compositions anticipated by this application will produce an iodine-mediated coloration that is dissipated within 3 hours. It is recognized by one skilled in the art that it may be useful for the compositions contemplated in this application to temporarily impart a color. For instance, it may be of use to a surgeon to view a color on skin prior to opening an incision. Such a coloration provides evidence that the site is disinfected.

The concentration of molecular iodine contemplated in this application ranges from 15 ppm up to 330 ppm within a pH range of 3.0 to 7.5. The preferred concentration of molecular iodine is from 25 ppm to 175 ppm. The most preferred concentration of molecular iodine is from 25 to 100 ppm.

Numerous methods known in the art can be utilized to form molecular iodine. For in situ generation of iodine from iodide the most common oxidants are active chlorine compounds and hydrogen peroxide. However, in the latter case a catalyst is necessary to speed up the formation of iodine. Other iodine generating compounds have been used including iodine pentoxide and tetraglycine hydroperiodide. Molecular iodine can also be generated by dilution of formulations that contain complexed iodine or by dissolution of elemental iodine as is done in several devices utilized for water disinfection.

Molecular iodine can be generated in situ in an aqueous medium by combining a source of peroxidase, a source of hydrogen peroxide and an iodide. This combination is known to be bactericidal. This bactericidal activity results from the enzymatic reaction that occurs when peroxidase, hydrogen peroxide and iodide react in solution at a controlled pH between pH 3.0 and 7.5. Peroxidase is known to effect the transfer of electrons from iodide to hydrogen peroxide. Hydrogen peroxide is converted into water by this reaction. The preferred oxidant of this invention is hydrogen peroxide. Any material that acts as a source of hydrogen peroxide when admixed in an aqueous environment is suitable for this application. The term "source of peroxide" for purposes of the present invention and as used herein shall mean any material alone or in combination which can serve as precursors for hydrogen peroxide including metal peroxides, percarbonates, persulphates, perphosphates, peroxyesters, urea peroxide, peroxyacids, alkylperoxides, acylperoxides and perborates. Alternately methyl, ethyl and other higher molecular weight peroxides can be used as a source of hydrogen peroxide but these are not preferred. Mixtures of two or more of these substances can also be used. The preferred concentration for hydrogen peroxide is between 0.001 and 0.1% in the final composition prior to initiation of the oxidation of iodide.

Suitable dry sources of iodide anion include sodium iodide and potassium iodide as well as other salts of iodide. Any compound that yields iodide anion upon dissolution in an aqueous environment is suitable for this application. The simple salts of iodide are preferred and have the advantage of being less costly. Additionally, they have a long shelf life in solid and liquid form.

The enzyme peroxidase is identified by the International Union of Biochemistry and the International Union of Pure and Applied Chemistry by the Enzyme Commission identification No. E.C. 1.11.1.7 although certain members of E.C. 1.11.1.8 can also be used. These classes of peroxidase can be obtained from a wide variety of sources including milk (lactoperoxidase), soy bean, and human leukocytes (myerloperoxidase). Within these two E.C. classes the further requirement for a suitable peroxidase as defined in this application is that it is capable of oxidizing iodide to iodine within the pH range of 3 to 7.5. The least expensive peroxidases suitable for this application is horseradish peroxidase and soybean peroxidase. It is anticipated that peroxidase that has been cloned from either horseradish, milk or human leukocytes or other sources will be suitable as a source of peroxidase for this application. Additionally, it has been observed that chemically modified peroxidase is suitable for use in this application. Modifications to the amino, carboxyl or carbohydrate moieties yield a suitable catalytic agent for inclusion in this application. The chemical modifications to peroxidase include cross-linking of enzyme molecules to each other, to solid surfaces or to other proteins. The chemical agents used for crosslinking include glutaraldehyde, maleimides, succinimides, carbodiimides, dicarboxylates, activated glycols, imidoesters, photoreactive azides and other agents known to one skilled in the art.

This application teaches that the concentration of triiodide should be minimized in order to minimize staining as demonstrated in the Examples of this disclosure. It may be necessary to formulate a composition at a particular pH and to incorporate certain additives that necessitate the incorporation of triiodide or promote the formation of triiodide. In other words, it is not always possible to eliminate triiodide from compositions of matter that contain substantial concentrations of molecular iodine. However, in accordance with the present invention it is necessary to carefully maintain the concentration of triiodide at below a preferred maximum level in order to minimize staining.

The complexing of molecular iodine by iodide ion has long been of major interest, and studies of this subject have used solubility, distribution and potentiometric, conductimetric, and spectrophotometric techniques. As a result, the factors that govern the formation of triiodide are well known in the art. In 1965, Ramette and Sandford (*Journal of the American Chemical Society*, Vol. 87(22), pages 5001–5) published a study, herein incorporated by reference, that provides an analysis of the factors that govern the formation of triiodide in addition to an empirical algorithm that accurately predicts the concentration of triiodide under a variety of conditions. As a practical matter, it is very useful to measure the concentration of molecular iodine as well as the concentration of triiodide and to correlate these measurements with the total mass of iodine known to be present in a composition.

The concentration of triiodide contemplated in this application ranges from 0 ppm up to a maximum of 700 ppm. The preferred concentration of triiodide should range from 0 ppm to 100 ppm. The most preferred concentration of triiodide should range from 0 to 50 ppm.

Complexed forms of iodine (e.g., polyvinylpyrrolidone iodine) other than triiodide can also stain skin. It is well known that 10% polyvinylpyrrolidone iodine forms a film on skin when it dries and that this film is highly colored. When the compositions of this invention also contain a complexed form of iodine, the sum of the concentrations of iodine complexed with organic compounds and triiodide should be limited to a maximum not to exceed 700 ppm under any circumstances. Iodide does not cause staining of skin. The concentration of iodide is not a critical aspect of staining but it will effect the concentration of molecular iodine and triiodide.

The types of compositions contemplated under this application include liquids, gels, creams, ointments and emulsions. The type of composition is not a determinative aspect of this application rather the absolute and relative concentration of molecular iodine and complexed iodine are the two most critical aspects of this invention. Examples of the different types of compositions are provided, by way of example, in the Examples section of this application. It is clear from these experiments that many different types of compositions are compatible with the teachings of this application.

Dermatological compositions frequently form a film over the epidermis. Such a film can provide added physical protection and serve to increase the emolliency of the topical composition. A good film-forming composition should be dermatologically acceptable and capable of application conveniently in a water based mixture which dries quickly on skin. The film should be water and body fluid resistant and permit facile transmission of water vapor. The film should adhere suitably to epidermis and be capable of facile removal from said epidermis. The film should be soluble in a dermatologically acceptable solvent such as water or a lower alkyl alcohol which may be used as or in a remover solution which could be employed to remove the film when desired. The film contemplated in this application is, when dry, about 0.002 mm to 0.05 mm thick.

The surfactants useful in the context of this application include anionic surfactants such as carboxylate, sulfonate, and sulfate materials including carboxylate surfactants such as potassium alkyloxycarboxylates, an alkyl sarcosinates, alkyl benzene sulfonates, alpha olefin sulfonates, and sulfonates with an ester amide or ether linkage. Additionally useful surfactant agents include sulfated alcohol, sulfated alcohol ethoxylates, sulfated alkyl phenols, sulfated carboxylic acid amides and esters, sulfated natural oils and fats as well as agents such as dioctyl ester sodium sulfosuccinic acid.

The thickeners useful in the context of the invention are preferably taken from the group consisting of alkyl celluloses, the alkoxy celluloses, xanthan gum, guar gum, polyorgano sulfonic acid and mixtures thereof. The thickeners are chosen based on compatibility with the other formulation ingredients and desired viscosity. Generally speaking the thickener should be present at a level of from about 0.01–10% by weight, and more preferable from about 0.1–1% by weight.

The penetrants useful in the context of the invention include isopropyl myristate, polyethylene glycol, and propylene glycol. Generally speaking the penetrant should be present at a level of from about 0.1 to 4% by weight.

Generally, any dispersible skin conditioning agent, humectants and emollients, known to those of skilled in this art may be used in the present invention. Preferred emollients to be used in the invention are taken from the group consisting of glycerin, propylene glycol, sorbitol, lanolin, lanolin derivatives, polyethylene glycol, aloe vera, Glucamate DOE 120 (a polyethoxylated glucose dioleate containing 120 ethoxy units in the polyethylene glycol moiety, available), Glucam E10 (a polyethoxylated methyl glucose containing 10 ethoxy units), Glucam E-20 (a polyethoxylated methyl glucose containing 20 ethoxy units in the polyethylene glycol moiety), Glucam P-10 (a polyethoxylated methyl glucose), Glucam P-20 (a polyethoxylated methyl glucose containing 20 propoxy units in the polyethylene glycol moiety), allantoin, alginates, monoester salts of sulfosuccinates, alphahydroxy fatty acids, esters of fatty acids, ceramides, and mixtures thereof. Broadly, the conditioning agents are used at a level of from about 0.5–20% by weight. The most preferred conditioning agents are mineral oil, glycerin and/or propylene glycol, and are usually employed at a level of from about 1–20% by weight, and more preferably from about 2–10% by weight.

Dye or pigment used in the compositions of the invention may be any organic or inorganic dye or pigment which is a chemically acceptable trace constituent on epidermal surfaces. Generally, dyes which are useful in the composition of this invention include 7 FD&C dyes available that are generally recognized as safe. Although any number of colorants may be used, these dyes are preferred due to their relative acceptability in various solid and liquid food systems. Generally, dyes or pigments used in the invention are present in a concentration ranging from about 0.001 to about 0.01 wt %.

Chelating agents or sequestrants can be useful stabilizing agents in the invention particularly when a complexed form of iodine is present. Commonly available chelating agents can be used in the invention including both inorganic and organic chelating agents. Organic chelating agents include alkyl diamine polyacetic acid, chelating agents such as EDTA (ethylenediamine tetracetic acid tetrasodium salt), acrylic acid and polyacrylic acid type stabilizing agents, phosphonic acid and phosphonate type chelating agents and others. Preferable organic sequestants include phosphonic acids and phosphonate salts including 1-hydroxy ethylidene-1, 1-diphosphonic acid, amino [tri(methylene phosphonic acid)], ethylene diamine [tetra(methylene-phosphonic acid)], 2-phosphonobutane-1,2,4-tricarboxylic acid as well as alkali metal salts, ammonium salts, or alkyl or alkanol amine salts including mono-, di- or triethanol amino salts. Inorganic chelating agents include commonly available polyphosphate materials such as sodium pyrophosphate, sodium or potassium tripolyphosphate along with cyclic or higher polyphosphate species. Preferably, such a sequestering agent is used at a concentration ranging from about 0.05 wt % to about 0.5 wt % of the composition.

Commonly available organic acids that can be used in the invention include benzoic acid, mandelic acid, sorbic acid, citric acid, lower alkanoic acids and their food-grade salts, such as the sodium potassium or ammonium salts thereof. These organic acids, their salts, or mixtures thereof are present in the composition in an amount between about 0.010 to 0.5 percent by weight, preferably from 0.050 to 0.20 percent by weight. The presently preferred organic acids are mandelic acid, benzoic acid and sorbic acid, with benzoic acid suitably present as sodium benzoate and sorbic acid suitably present as the free acid. Each of these acids, or their salts, and others, alone or in combinations, can be incorporated into the compositions contemplated in this invention.

Commonly available film forming agents that can be used in the invention include polyvinylpyrrolidone (PVP), PVP derivatives like alkylated PVP, PVP copolymers like PVP/dimethylaminoethylmethacrylate/polycarbamyl/polyglycol ester, Polaxomers, polyethylene glycol, polyvinyl alcohol, polysulfonic acid, water soluble cellulose derivatives, acrylate copolymers such as acrylate/hydroxyester acrylate copolymers, collagen and collagen derivatives, keratin, polyquaternium compounds, interpenetrating polymers of polycrylic acid and a block terpolymer of propylene oxide and ethylene oxide with reverse thermal gelation properties, polyvinyl methacrylate derivatives and tosamide epoxy resins.

Various formulations anticipated under the teachings of this application may require two separate phases or components. This is understood and it is incorporated into the teachings of this application. Two components products that are activated prior to use by admixture are commonly available. Cheeseborough Pond's USA Company (CPUSA) has successfully introduced Mentadent© toothpaste. Consequently, CPUSA has commercialized a mouthwash and handcream that both rely upon admixture prior to use. In many instances, pharmacists compound a product and package it into a dispenser for subsequent use by the consumer. It is anticipated that many of the potential formulations contemplated under this application will fall into such a category.

Any method to generate molecular iodine, in situ, may be used to formulate a dermatological non-staining topical iodine antimicrobial composition in accordance with the present invention including the method of generating molecular iodine taught in copending patent application Ser. No. 08/960,149 filed Oct. 29, 1997, U.S. Pat. No. 5,885,592, the disclosure of which is herein incorporated by reference. As taught in the foregoing patent application molecular iodine may be generated, in situ, by combining an iodine reductant in concert with an oxidant iodine species having a positive oxidation state and a buffering agent for causing oxidation-reduction reactions to occur in which the iodine reductant is reduced to molecular iodine or in which the oxidant iodide species is oxidized into molecular iodine. The iodine reductant may be selected from the group consisting of iodide, sodium thiosulfate, ascorbate, lactose, reducing sugars and imidazole whereas the oxidant iodine species may be selected from the group consisting of hydrogen peroxide, iodate, alkali salts of peroxide such as calcium peroxide, peroxidase, ascorbic acid and/or other pharmaceutically acceptable organic acids with an oxidation potential greater than −0.54 electron volts. The preferred formulation combines an iodide and an iodate with a suitable buffer to control pH preferably in two phases with the first phase incorporating the iodate and iodide in a first buffer to form a basic pH and with the second phase being the activator phase which is highly buffered with an acidic buffer such as, for example, citric acid, phosphoric acid and phthallic acid. The iodide in the preferred formulation may be selected from the group consisting of sodium iodide, potassium iodide, ammonium iodide, calcium iodide, and magnesium iodide and the iodate of such formulation may be selected from the group consisting of calcium iodate, magnesium iodate, potassium iodate, and sodium iodate. The preferred range of the iodide to iodate species in the preferred formulation is from $\frac{1}{3}$ to $\frac{1}{12}$. The pH of the iodate/iodide phase should be no less than 8.0 and preferably greater than 8.5. The iodate/iodide phase can assume a diverse range of compositions: liquid, gel, ointment or cream. The critical aspect of the iodate/iodide phase is that these two active agents are stable. Prior to use, the iodate/iodide phase is combined with a second activator phase. The activator phase is highly buffered at a pH that is less than 5.0. The pH of the mixture of these two phases must be controlled such that the final pH is 5.0 or less. As a consequence of altering the pH environment, molecular iodine is generated from the iodate and iodide. An example of such a composition is given in Example 12 below.

The following examples are illustrative of the teachings of this application and are not meant to limit the invention in any manner.

EXAMPLES

1. This experiment was performed to demonstrate that molecular iodine does not necessarily stain human skin and when it does impart color to epidermal tissue, it does so in a rapidly reversible manner. Elemental iodine was weighed on an analytical balance and dissolved in one liter of water that had been acidified with 2 drops of 0.1N hydrochloric acid. The concentration of molecular iodine in the water was confirmed by potentiometric analysis (Gottardi, W., 1983. *Fresenius Z. Anal. Chem.*, Vol. 314, pages 582–585).

Samples were also titrated with thiosulfate to determine that at least 95% of the theoretical yield of titratable iodine was in the form of molecular iodine as opposed to triiodide. The concentration of molecular iodine was varied from 25 ppm to 330 ppm.

One dram vials (Kimble catalog # 60931) were used to deliver 4 mL of the room temperature iodine solutions samples. The vials were placed on the forearm of a subject and then the forearm was inverted to initiate contact of the sample with the iodine solution. The contact area was a circle with a diameter of 1.3 cm. The samples were held on the arm for 30 seconds at room temperature. Three different subjects were used for this experiment. Immediately after the 30 second contact time the arms of the subjects were examined for stains; 10 minutes after the end of the contact time all subjects arms were examined for stains again. The results of these experiments are shown in Table 1 below and demonstrate that molecular iodine does not stain skin irreversibly.

For the purposes of this application, two different parameters were used to characterize the color and intensity of the term stain. The hue of the color imparted to skin was characterized by using the Pantone Color Matching System (Pantone Color Specifier, Pantone Inc., Carlstadt, N.J.) which allows comparison with 1,012 defined colors on two types of paper. Stains from triiodide were matched to the Pantone color chip No. 152C. Short-lived coloration from molecular iodine were matched to the Pantone color chip 1 375C.

TABLE 1

Coloration of Human Skin by a 30 Second Exposure to Molecular Iodine

| Concentration | 25 ppm | | 50 ppm | | 100 ppm | | 200 ppm | | 300 ppm | |
|---|---|---|---|---|---|---|---|---|---|---|
| Min. post contact | 0 | 10 | 0 | 10 | 0 | 10 | 0 | 10 | 0 | 10 |
| Subject 1 | N | N | N | N | N | N | S | N | S | N |
| Subject 2 | N | N | N | N | L | N | S | N | S | L |
| Subject 3 | N | N | N | N | L | N | S | N | S | L |

Key to Table 1.
N = no visible staining
L = light staining barely noticeable
S = a clearly visible coloration The intensity of any coloration on skin was characterized by applying an aqueous solution of known concentrations of a food dye, Brown No. 3 (Crompton & Knowles, Mahwah, N.J.—Code DP935159), for 10 seconds using the method described above for application of iodine. Brown No. 3 was applied to the skin at concentrations that ranged from 500 ppm to 30 ppm and the intensity of the color from Brown No. 3 was compared to the intensity of coloration from iodine compositions. For instance, the intensity of color 10 minutes after a 30 second contact with a 600 ppm aqueous triiodide solution was equivalent to the color from a 10 second exposure to a 250 ppm Brown No. 3 solution. In contrast, the intensity of color 10 minutes after a 30 second contact with a 300 ppm aqueous molecular iodine solution was equivalent to the color from a ten second exposure to a 30 ppm Brown No. 3 solution which is barely discernible.

2. Three samples from Example 1 were used to confirm that molecular iodine will penetrate into skin and remain in the skin for a prolonged time period.

Application of the iodine solution onto skin was performed as described in Example 1 above with the exception that the contacted area was flushed with water for 15 seconds immediately after following contact between the iodine solution and skin. The method of Gottardi (*J. Hosp. Infect.*, 1995, Vol 29, pages 9–18) were used to measure the amount of molecular iodine coming out of the skin. Briefly, 1 mL of a diethyl-p-phenylenediamine (DPD) solution was placed concentrically onto the exposed area of skin and left there for 30 seconds. This solution was then transferred to a 1 cm cuvette and the absorbance was read at 553 nm. Control values were obtained by contacting the DPD solution to an unexposed area on the forearm of each subject. Control values were subtracted from the experimental measurements. Iodine solutions containing 50 ppm, 150 ppm and 300 ppm of molecular iodine were used for this example. Two measurements were made (one measurement of each forearm) at each iodine concentration on all three subjects. The average reading from all three subjects is shown in Table 2 as a function of time

TABLE 2

Diffusion of Iodine from Skin Post Application

| Time (minutes) after application of iodine | 3 | 6 | 20 | 60 | 90 | 120 | 240 | 660 |
|---|---|---|---|---|---|---|---|---|
| Mean absorbance 50 ppm I$_2$ | 0.068 | 0.174 | 0.192 | 0.186 | 0.131 | 0.083 | 0.066 | 0.029 |
| Mean absorbance 150 ppm I$_2$ | 0.327 | 0.311 | 0.487 | 0.533 | 0.501 | 0.462 | 0.369 | 0.204 |
| Mean absorbance 300 ppm I$_2$ | 0.784 | 0.650 | 1.115 | 0.931 | 0.775 | 0.643 | 0.579 | 0.408 |

The conclusion from this experiment is clear. Molecular iodine maintains chemical activity on and in the skin even under conditions where there is no skin coloration from molecular iodine.

3. This experiment was performed to demonstrate that triiodide stains epidermal tissue in a manner that is not rapidly reversible. Solutions of triiodide were prepared by dissolving elemental iodine into oxygen-free solutions of sodium iodide that were at a pH of 4.5. A molar excess of iodide was used. Based on thiosulfate titrations, potentiometric measurements of iodine and ion selective electrode measurements of iodide ion, essentially all of the elemental iodine was converted into triiodide. Solutions of triiodide were made that varied from 100 to 25,000 ppm. Four mL of each sample was transferred to a 1.0 dram vial (Kimble catalog #60931) at room temperature and placed on the forearm of a subject and then the forearm was inverted to initiate contact of the sample with the triiodide solution. The samples were held on the arm for 10 seconds.

The contact areas were checked for stains at 10 minutes and 3 hours after exposure. A definite coloration of the epidermis was evident 3 hours after contact with triiodide at concentrations from 25,000 to 700 ppm. At 700 ppm triiodide the degree of color was minimally discernable. At 100 ppm triiodide staining was present at three hours but it was not visibly noticeable.

4. This experiment was performed to demonstrate the relative staining properties of compositions that contain different concentrations and ratios of molecular iodine/triiodide. Dilutions of strong Lugol's solution were made and characterized. Iodide ion was measured using an iodide ion selective electrode, molecular iodine was measured using the potentiometric method of Gottardi and thiosulfate titrations were used to calculate the concentration of triiodide. Four mL of each sample was transferred to a one-dram vial at room temperature and placed on the forearm of a subject and then the forearm was inverted to initiate contact of the sample with the triiodide solution. The samples were held on the arm for 10 seconds. Observations were made of the contacted area at 10 seconds and three hours.

Table 4 below shows the results of these experiments. The data indicates that there are preferred ranges for both molecular iodine and triiodide. Controlling the concentrations of these species within those ranges can yield compositions that provide defined levels of staining.

TABLE 4

Staining of Human Skin by Various Concentrations and Ratios of Molecular Iodine to Triiodide (10 second exposure)

| Observation | Iodide ppm | Molecular Iodine ppm | Triiodide ppm | pH |
|---|---|---|---|---|
| Dark stain present longer than 3 hours. | 25,670 | 103 | 11,929 | 6.12 |
| Dark stain present longer than 3 hours. | 15,122 | 123 | 6,980 | 6.08 |
| Dark stain present longer than 3 hours. | 10,684 | 154 | 4,695 | 5.74 |
| Easily visible stain present longer than 3 hours. | 5,782 | 162 | 2,411 | 5.54 |
| Some coloration at three hours. | 1,452 | 124 | 508 | 5.32 |
| No staining at 10 seconds. | 224 | 56 | 51 | 5.01 |

5. This experiment was performed to demonstrate that molecular iodine that diffuses into the skin can inactivate pathogens that are on or in the skin. A saturated solution of molecular iodine was prepared at a pH of 4.5. The concentration of molecular iodine was measured to be 320 ppm and the concentration of triiodide was determined to be less than 5 ppm. A 1.0 dram vial containing four mL of the saturated iodine solution was contacted with the forearm of a subject and then the forearm was inverted to initiate contact of the sample with the molecular iodine solution. The samples were contacted with the arm for 30 seconds. After contact the treated arm was flushed with water for 15 seconds and dried.

Six circular skin areas on two different subjects that were treated with the saturated iodine solution were marked immediately after treatment with a water-resistant ink. Two hours after contact each area was inoculated with 25 mL of a 1:100 dilution of a 48 hour soy-trypticase culture of *Staphylococcus aureus*. Ninety minutes after inoculation the mouths of sterile 25 mL flasks filled with 2 mL of soy-trypticase with 2% Tween 80 were placed over the marked skin areas. The flasks were gently shaken for 1 minute and a colony count was performed on blood agar plates after incubation at 37° C. for 48 hours. The residual biocidal effect from skin associated molecular iodine was determined by subtracting the log of the colony counts from the areas of skin that were contacted with iodine from the controls (log colony count from untreated skin). The average difference in colony counts between treated and untreated skin was 2.4 logs. Efficacy was also demonstrated when this experiment was repeated using *Staphylococcus epidermidis, Streptococcus agalactica, Candida albicans, Salmonella typhimurium,* and *Pseudomonas aeruginosa*. The smallest log reduction was observed with Pseudomonas aeruginosa and was equal to 0.5 logs. When a solution that contained 700 ppm of triiodide, but no molecular iodine, was used in this experiment, no measurable reduction in the concentration of pathogens was observed.

This experiment demonstrates that non-staining iodine can serve as an efficacious biocide on the skin surface for a prolonged time period. That is to say, it is evident from this experiment that a sufficient degree of kill on and in the epidermis is achieved from the use of molecular iodine as described this application. This experiment demonstrates that molecular iodine works independent of triiodide consistent with previous observations in the art (U.S. Pat. No. 5,419,902; U.S. application Ser. No. 08/293,283, U.S. Pat. No. 5,629,024; U.S. application Ser. No. 08/551,478, U.S. Pat. No. 5,639,481; U.S. application Ser. No. 08/684,334, U.S. Pat. No. 5,648,075) which are incorporated herein.

6. This experiment was performed to demonstrate that the invention described in this application is compatible with an oil/water emulsion. The raw materials included in this mineral oil emulsion are shown in Table 6. The materials for this composition were selected without any consideration or optimization of the materials with respect to the individual components used. It is reasonably expected by one skilled in the art that this composition is representative of a broad class of oil/water emulsions which are incorporated herein. It was decided to formulate a highly emollient dermatological composition for the treatment of bacterial infections of the skin. The formulation and the procedure to make this creamy emulsion is shown below.

TABLE 6

Raw Materials in Cream Emulsion

| Composition Number | Percent by Weight | Material | Chemical Name |
|---|---|---|---|
| 1 | 75.0 | DI Water | Water |
| 1 | 0.3 | Liposorb L-20 | Polysorbate-20 |
| 1 | 0.1 | Natrosol 250H HR | Hydroxyethylcellulose |
| 2 | 15 | Petrolatum | Petrolatum |
| 2 | 3.5 | Mineral Oil 130 | Mineral Oil 130 |
| 2 | 0.3 | Lanette O | Cetearyl Alcohol |
| 2 | 3.7 | Brij 72 | Steareth-2 |
| 2 | 2.2 | Myverol 18-04 | Hydrogenated Palm Glyceride |

The procedure to make the emulsion follows: heat the water in Composition #1 to 76° C. and slowly add Natrosol, disperse the Natrosol thoroughly then add the Liposorb L-20 under propeller mixing. Mix the raw materials in Composition #2 and then heat to 78° C. Slowly add Composition #2 at 78° C. to Composition #1 at 76° C. under homogenizer mixing. Homogenize for 5–10 minutes or until emulsification is complete. Remove the homogenizer and allow the mixture to cool to 25° C. under propeller mixing.

This base composition was used to prepare two separate components that yield molecular iodine when combined. Horseradish peroxidase and iodide were mixed with the cream in one compartment and hydrogen peroxide was placed in a second compartment. The cream (75 grams) was mixed with $H_2O_2$ so that the final concentration of hydrogen peroxide was 0.6%. Peroxidase and sodium iodide were mixed in a 3/1 ratio and 2.5 grams of this mixture was combined with 97.5 grams of the cream. Five mL of the cream containing hydrogen peroxide and five mL of the cream containing peroxidase/iodide were mixed and the concentration of total iodine was determined to be 720 ppm. The concentration of sequestered iodine, including triiodide, was 500 ppm and the concentration of molecular iodine was approximately 220 ppm.

Immediately after mixing the two components, 0.5 mL of the mixture was immediately applied to a square 2 inch section of the forearm of three human subjects. The DPD method to detect iodine out-gassing described in Example 2 was used to confirm that iodine was associated with the area of skin that had been treated with the cream. Iodine was detected immediately after sample application and at 1, 3 and 6 hours post treatment; at 1 hour the DPD absorbance was 0.624, at 3 hours it was 0.403, and at 6 hours it was 0.286.

7. A topical gel composition was developed to determine the rate of penetration of molecular iodine into skin. Several different carriers were evaluated to determine their ability to deliver iodine into skin. These carriers are Carbopol 941 (1%), polysulfonic acid (7.5% PSA), hydroxypropyl methyl cellulose (5% HPC or Methosil), carboxymethyl cellulose (1% CMC), sodium alginate (2%) and Sepigel 305 (3%). As an initial screen the relative rate of disappearance of iodine from these formulations into skin was evaluated visually. A known amount of a formulation was placed on the top of a subject's hand and spread into a thin layer. After one minute, a known amount of this sample was removed and assayed for iodine content. Two vehicles, PSA and CMC, showed rapid disappearance of iodine. The disappearance of iodine is due to iodine penetration into the skin since the control (i.e., a formulation spread over a glass slide) showed no loss of iodine over the same time period.

The hydroxypropyl methyl cellulose gel was formulated to deliver different concentrations of iodine. The four different gel compositions that were prepared contained concentrations of total iodine that varied between 140 to 500 ppm. The gels were contacted to the forearm of the identical volunteer and iodine out-gassing was measured 5 minutes after contact. The results are shown below: three mL of each formulation was contacted with and rubbed into the forearm of human subjects and their skin was observed for staining. No staining was observed in any instance. Iodine out-gassing was measured for each concentration of iodine in the Methosil gel using the method described in Example 6. The results of these measurements are shown below in Table 7. Iodine clearly entered into the skin and was back-diffusing out of the skin.

TABLE 7

Iodine Determination from Skin 5 Minutes Post Treatment with HPC Gels

| Total Iodine (ppm) | 140 | 250 | 400 | 500 |
|---|---|---|---|---|
| Absorbance (DPD) | 0.306 | 0.395 | 0.637 | 0.945 |

8. A viscous barrier teat dip was formulated using the conditions described in this application. The teat dip was formulated in two separate liquid components. One component contained lactoperoxidase and iodide. The other component contained hydrogen peroxide. When the two components were mixed in equal volumes 300 ppm of total iodine was generated with 200 ppm of molecular iodine being formed. The fully activated teat dip contained 0.4% polyvinyl pyrrolidone, 10% glycerin, 2% benzoic acid, 2% polyethylene glycol, 0.2% xanthan gum, 0.03% sodium lauryl sulfate, 0.01% silicone antifoam, 0.1% mixture of three food dyes and 3% Rheothick 80–11. The composition had a relatively high viscosity and provided significant film-forming capability with resultant protective properties.

9. The rate of healing wound was measured using Yorkshire pigs, weighing approximately 20 k. The pigs, were allowed to acclimate for 1 week before 50 to 100 shallow wounds measuring 7 mm wide and 10 mm long by 0.3 mm deep were made in the paravertebral and thoracic areas with an electric dermatome. The wounds were treated daily for the duration of the study with normal saline or a solution of iodine. Three times daily, 1.0 mL of these iodine solutions were applied to the wound sites and held there by an occlusive bandage. Beginning on day 4 after wounding and each day thereafter, 5 to 6 wounds and the surrounding normal skin were excised, and harvested specimens were incubated with 0.5 molar sodium bromide at 37° C. for 24 hours, and then the epidermis was separated from the dermis. The epidermal sheet was examined for defects. Wounds were considered healed if there were no defects in the epidermis, and wounds were considered not to be healed if there were one or more defects.

The two iodine compositions were generated by oxidizing iodide with horseradish peroxidase and hydrogen peroxide. The compositions contained either 47 or 175 ppm of free molecular iodine and the corresponding concentration of thiosulfate titratable iodine was 102 and 280 ppm respectively. The percentage of healed wounds was determined post wounding from day 4 to 7. By day 8, 100% of the wounds were healed in all three treatment groups. There was not a material difference in the rate of wound healing among the three treatment groups at day 7 as shown below.

TABLE 9

Percentage of Wounds Healed versus Time

| Molecular Iodine (ppm) | Titratable Iodine (ppm) | Free Molecular Iodine (ppm) | % Wounds Healed Day After Wounding | | | |
|---|---|---|---|---|---|---|
| | | | 5 | 6 | 7 | 8 |
| $3.14 \times 10^{-3}$ | 280 | 175 | 0 | 0 | 50 | 100 |
| $1.26 \times 10^{-3}$ | 102 | 47 | 0 | 0 | 50 | 100 |
| 0 (Saline) | 0 | 0 | 0 | 0 | 71 | 100 |

10. The cream described in Example 7 above was used to treat the skin disease caused by *Propionibacterium acnes*. Prior to administration of the cream, quantitative bacteriologic cultures were obtained from the cheeks (two test sites) of four male subjects with acne. After one week of treatment cultures were again taken. An area of 3.9 cm$^2$ were outlined by holding a sterile glass cylinder (diameter 2.23 cm) against the skin. The cheeks of subjects were cleansed by wiping for 30 seconds with a sterile gauze soaked with 0.1% Triton X-100 to remove surface debris and bacteria. Wash solution (1.0 mL of 0.1% Tween-80 in 0.075 molar phosphate buffer, pH 7.9) was pipetted into the cylinder and each area scrubbed with moderate pressure for 1 minute using a sterile Teflon stir-bar. The wash fluid was aspirated, replaced with 1.0 mL of fresh wash solution, and the scrub repeated. The two 1.0 mL samples were combined and diluted serially in 0.05% buffered Tween-80 on Schadler agar and cultured anaerobically for 7 days. *P. acnes* were identified by colony morphology and susceptibility to *P. acnes* bacteriophage.

The number of *P. acnes* bacteria per square centimeter was calculated from plate counts and expressed as a logarithm. Subjects applied cream to their cheeks three times daily. The difference between the initial level of *P. acnes* and the level after one week of treatment was expressed as the log reduction in counts. The mean value of *P. acnes* at the start of the study was 6.18 or $1.51 \times 10^6$ cfu/cm$^2$. The mean value after one week of treatment was 4.12 which equals a log reduction of *P. acnes* of 2.06.

11. The 300 ppm samples of molecular iodine described in Example 1 was used to confirm that molecular iodine will penetrate into skin and permeate into the skin to provide sub dermal tissue penetration.

Application of the iodine solution onto skin was performed as described in Example 1 above with two exceptions: (1) the contacted area was flushed with water for 15 seconds immediately after following contact between the iodine solution and skin and (2) the sample was applied to the skin once every 2 hours over a six hour time period (4 applications).

Twenty-four hour urine samples were collected on three subjects for the day immediately prior to the experiment. Twenty-four hour urine samples were collected on three subjects on the day of the experiment. The urine samples were analyzed to determine their total iodine content. Urinary concentrations of total iodide were measured by utilizing the reduction-oxidation reaction between ceric ioni and arsenite ion catalyzed by iodide. The concentration of iodide in the sample is therefore proportional to its catalytic activity. Samples along with standards and controls in a urine matrix were first digested with chloric acid. Arsenious acid was added, the samples were transferred to an autoanalyzer, ceric ammonium sulfate was added "on line" and the optical transmission was measured spectrophometrically at 420 nm. The reagents used were: perchloric acid ($HClO_4$), 70%–72%, ACS grade; sulfuric acid ($H_2SO_4$), ACS grade; arsenic trioxide ($AS_2O_3$), ACS grade; sodium chromate ($Na_2CrO_4$), ACS grade; potassium chlorate ($KClO_3$), purified; ceric ammonium sulfate $(NH_4)_4Co(SO_4)_4 \cdot 2H_2O$; sodium chloride (NaCl), ACS grade; potassium iodate; and distilled water. 200 $\mu$L of sample, 200 $\mu$L of a Low control and 100 $\mu$L of the High control were transferred into appropriately numbered tubes. 1.0 mL of a 0.02, 0.04, and 0.06 $\mu$g/mL iodate standards were transferred into appropriately numbered tubes. Nothing was added to the 0.0 $\mu$g/mL tube. 3.0 mL of a 28% chloric acid solution was added to each tube. Samples, controls, and standards were incubated at 105° C.–110° C. using a sand bath heater. Digestion was completed in approximately 2–2.5 hours. The end point of the digestion was the formation of chromium trioxide crystals (red crystals). Samples were allowed to cool to room temperature. 2.1 mL of arsenious acid solution was added to each tube and mix. Approximately 2.0 mL of each processed sample was added to autoanalyzer cups (2 mL volume) and they were placed on the sampler. Prior to allowing the samples to proceed through the autoanalyzer system for the color reaction, a screen test on the left over portion of the test sample was performed in order to determine if a sample contained a grossly elevated iodine content. This was done to avoid contamination of the autoanalyzer system. The screen test is performed by adding 1 drop of the ceric ammonium sufate reagent to each tube. If the yellow color fades to colorless (clear) within 1.5 minutes, the iodine content is too high to be measured. These high samples were removed from the sampler and discarded. They were then repeated on further dilution. After the screening procedure was completed, the samples were run through the autoanalyzer at a sampling rate of 40 samples per hour with the temperature controlled water bath set at 32° C.±0.1° C. The % transmission was recorded and the concentration of iodine in each sample was determined by comparison to the standards.

TABLE 11

Sub Dermal Penetration of Iodine as Measured by Iodine Analysis of Urine

| | 24 Hour Urine (ug iodine) | |
|---|---|---|
| | Prior to $I_2$ Application | Post $I_2$ Application |
| Subject 1 | 95 | 647 |
| Subject 2 | 114 | 846 |
| Subject 3 | 106 | 741 |

The conclusion from this experiment is clear. Molecular iodine maintains chemical activity on the surface of skin even under conditions where there is no skin coloration from molecular iodine.

12. A gel formulation was prepared that delivered 200 ppm of molecular iodine when activated. This composition was prepared using a Carbopol gel (type 980) as the gelling agent. The components used to generate molecular iodine were iodide and iodate. Iodide and iodate were formulated into a single gel phase. A second buffer gel phase was formulated such that upon admixture of an equal volume of the two phases (iodide/iodate phase; buffer phase), 200 ppm of molecular iodine was formed. The rate of formation of molecular iodine was monitored and the formulation was intended to form 200 ppm of molecular iodine within 60 seconds after admixture.

The iodide/iodate phase contained the following components: Carbopol 980 at 1.00%; EDTA at 0.10%; glycerin at 10%; boric acid at 0.10%; 1.4% sodium hydroxide; 0.06% sodium iodide; and 0.20% sodium iodate. The pH of this gel phase was adjusted to 10.3. The buffer phase container the following chemicals: 4% Carbopol 980; 12% citric acid; 0.10% EDTA; 10% glycerin; and 0.10% boric acid.

An equal volume of the two gels was mixed and the amount of molecular iodine was measured at 0, 30, 60, 90 and 150 seconds. Molecular iodine was measured by extraction of the molecular iodine into chloroform and subsequent measurement of the visible absorbance at 520 nm. The percent conversion of iodide into molecular iodine (i.e., yield) was determined and is reported the table below.

Formation of molecular Iodine in Carbopol 980 versus Time

| Min. | $I_2$ ppm | $I_2$ Yield |
|---|---|---|
| 0 | 0 | 0 |
| 0.5 | 205 | 67 |
| 1 | 204 | 66 |
| 1.5 | 202 | 66 |
| 2.5 | 215 | 70.5 |

Fifty mL of each gel phase was mixed in a glass flask and a ground glass stopper was placed in the top of the flask to prevent loss of molecular iodine to the atmosphere. The concentration of molecular iodine was measured in this sample at day 1, 3, 7, 14 and 21. This study was performed to demonstrate that the compositions of this application can demonstrate stability after being activated. The results of these measurements are shown in the table below.

| Molecular Iodine versus Time in Carbopol Gel | | | | | |
|---|---|---|---|---|---|
| Day Number | 0.04 | 3 | 7 | 14 | 21 |
| ppm $I_2$ | 212 | 204 | 223 | 205 | 198 |

What is claimed is:

1. A method of topically treating skin without irritating the skin and without leaving a visible skin discoloration noticeable to the naked eye after a duration not exceeding three hours comprising the step of, applying an iodine composition to the surface of the skin, said iodine composition comprising molecular iodine in a concentration above at least 15 ppm and at least one other iodine species selected from the group consisting of triiodide and complexed iodine and wherein the total concentration of the triiodide component present in the iodine composition is less than about 700 ppm.

2. A method as defined in claim 1 wherein said molecular iodine is present in a range of from 15 ppm to 330 ppm.

3. A method as defined in claim 2 wherein said molecular iodine is present in a range of from 25 ppm to 175 ppm.

4. A method as defined in claim 1 wherein said duration does not exceed 10 minutes.

5. A method as defined in claim 2 wherein said molecular iodine is generated in situ.

6. A method as defined in claim 5 wherein said molecular iodine is generated using an aqueous composition consisting essentially of a source of peroxidase, a source of hydrogen peroxide, an iodide and a buffer to control the pH of the composition between a pH of 4.0 and 7.5.

7. A method as defined in claim 6 for the treatment of fungal and viral infections of the skin wherein said iodine composition further comprises an anionic surfactant selected from the group consisting of carboxylate, sulfonate, a carboxylate surfactant, an alkyl sarcosinate, alkyl benzene sulfonate, alpha olefin sulfonate and a sulfonate with an ester amide or ether linkage.

8. A method as defined in claim 7 wherein said iodine composition further comprises dispersible skin conditioning agents selected from the group consisting of film forming agents, penetrants, organic acids, humectants and emollients.

9. A method as defined in claim 7 wherein said iodine composition further comprises a sequestering agent.

10. A method as defined in claim 8 wherein said emollient is selected from the group consisting of glycerin, propylene glycol, sorbitol, lanolin, polyethylene glycol, aloe vera, Glucamate DOE 120 (a polyethoxylated glucose dioleate containing 120 ethoxy units in the polyethylene glycol moiety, available), Glucam E10 (a polyethoxylated methyl glucose containing 10 ethoxy units), Glucam E-20 (a polyethoxylated methyl glucose containing 20 ethoxy units in the polyethylene glycol moiety), Glucam P-10 (a polyethoxylated methyl glucose), Glucam P-20 (a polyethoxylated methyl glucose containing 20 propoxy units in the polyethylene glycol moiety), allantoin, alginates, monoester salts of sulfosuccinates, alphahydroxy fatty acids, esters of fatty acids, ceramides, and mixtures thereof.

11. A method as defined in claim 8 wherein said organic acids are selected from the group consisting of benzoic acid, mandelic acid, sorbic acid, citric acid, lower alkanoic acids and sodium, potassium or ammonium salts thereof.

12. A method defined in claim 8 wherein said film forming agents are selected from the group consisting of:
polyvinylpyrrolidone (PVP), alkylated PVP, PVP/ dimethylaminoethylmethacrylate/polycarbamyl/ polyglycol ester, polaxomers, polyethylene glycol, polyvinyl alcohol, polysulfonic acid, water soluble cellulose, acrylate/hydroxyester acrylate copolymers, collagen and collagen derivatives, keratin, polyquaternium compounds, interpenetrating polymers of polyacrylic acid and a block terpolymer of propylene oxide and ethylene oxide with reverse thermal gelation properties, polyvinyl methacrylate derivatives and tosamide epoxy resins.

13. A method as defined in claim 2 wherein the iodine composition applied to the skin is within a pH range of 3.0 to 7.5.

14. A method as defined in claim 13 wherein the triodide concentration is less than about 100 ppm.

15. A method as defined in claim 14 for the treatment of fungal and viral infections of the skin wherein said iodine composition further comprises an anionic surfactant selected from the group consisting of carboxylate, sulfonate, a carboxylate surfactant, an alkyl sarcosinate, alkyl benzene sulfonate, alpha olefin sulfonate and a sulfonate with an ester amide or ether linkage.

* * * * *